(12) United States Patent
Bitter et al.

(10) Patent No.: US 9,709,487 B2
(45) Date of Patent: Jul. 18, 2017

(54) METHOD FOR MEASURING THE CONCENTRATION OF A GAS COMPONENT IN A MEASURING GAS

(71) Applicant: Siemens Aktiengesellschaft, Munich (DE)

(72) Inventors: Ralf Bitter, Karlsruhe (DE); Thomas Hankiewicz, Karlsruhe (DE); Christoph Wolfgang Marquardt, Karlsruhe (DE); Adrian Mucha, Karlsruhe (DE); Jan Nygren, Göteborg (SE); Kai-Uwe Pleban, Stutensee (DE); Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 174 days.

(21) Appl. No.: 14/601,729

(22) Filed: Jan. 21, 2015

(65) Prior Publication Data

US 2015/0204779 A1    Jul. 23, 2015

(30) Foreign Application Priority Data

Jan. 22, 2014   (EP) .................................. 14152041

(51) Int. Cl.
G01N 21/39    (2006.01)
G01N 33/00    (2006.01)
G01J 3/433    (2006.01)

(52) U.S. Cl.
CPC ............. G01N 21/39 (2013.01); G01J 3/433 (2013.01); G01N 33/0062 (2013.01); G01N 2021/399 (2013.01)

(58) Field of Classification Search
None
See application file for complete search history.

(56) References Cited

U.S. PATENT DOCUMENTS 5,969,825 A    10/1999    Silver
6,147,351 A *  11/2000    Huiku ................ G01N 21/0303
                                                     250/343

(Continued)

FOREIGN PATENT DOCUMENTS

CN    101646934    2/2010
EP    1927831 A1   6/2008

(Continued)

OTHER PUBLICATIONS

Goldenstein et al; "Fitting of calibration-free scanned-wavelength-modulation spectroscopy spectra for determination of gas proberties and absorption lineshapes"; Applied optics, Optical Society of America; vol. 53; No. 3; pp. 356-367; ISSN: 0003-6935; DOI: 10.1364/A0.53.000356; XP001587490; 2014; US; Jan. 20, 2014.

(Continued)

Primary Examiner — Kara E Geisel
Assistant Examiner — Amanda Merlino
(74) Attorney, Agent, or Firm — Cozen O'Connor

(57) ABSTRACT

A method for measuring the concentration of a gas component in a measuring gas. An absorption line of the gas component is varied as a function of the wavelength of the light of a wavelength-tunable light source within a periodically sequential scanning interval. The absorption line of the gas component is modulated with a frequency ($f_0$). Modulated light is guided through the measuring gas onto a detector. A measurement signal generated by the detector is demodulated upon determining a harmonic ($nf_0$) of the frequency ($f_0$). A measurement result is produced by fitting a setpoint curve to the profile of the demodulated measurement signal. Both demodulated measurement signal and setpoint cure are filtered with the aid of the same filter function. The filter function is operative to suppress noise signal components of the demodulated measurement signal that disturb both signal components of the demodulated measurement signal and the setpoint curve.

2 Claims, 2 Drawing Sheets

(56) References Cited

U.S. PATENT DOCUMENTS

2004/0223158 A1 11/2004 Thorsen
2008/0137084 A1 6/2008 Kluczynski
2011/0228371 A1 9/2011 Larking

FOREIGN PATENT DOCUMENTS

EP 1475618 B1 12/2008
EP 2336738 A1 6/2011
EP 2455733 5/2012

OTHER PUBLICATIONS

Werle et al; "Real-time signal-processing consepts for trace-gas analysis by diode-laser spectrocopry", Optical engineering, SOC. of photo-optical instrumentation engineers; vol. 33; No. 9; pp. 3093-3104;ISSN: 0091-3286; DOI: 10.1117/12.176262; XP000466562; 1994; Sep. 1, 1994.
Sun et al; "Analysis of calibration-free wavelength-scanned wavelength modulation spectroscopy for practical gas sensing using tunable diode lassers"; Measurement science and technology; IOP; vol. 24; No. 12; pp. 125203; ISSN: 0957-0233; DOI: 10.1088/0957-0233/24/12/125203; XP020254118; 2013; GB; Oct. 29, 2013.
Office Action dated Mar. 3, 2017 which issued in the corresponding Chinese Patent Application No. 2015100301696.

* cited by examiner

METHOD FOR MEASURING THE CONCENTRATION OF A GAS COMPONENT IN A MEASURING GAS

BACKGROUND OF THE INVENTION

1. Field of the Invention

The application generally relates to a method for measuring the concentration of a gas component in a measuring gas by a gas analyzer. An absorption line of the gas component is varied as a function of the wavelength of the light of a wavelength-tunable light source within a periodically sequential scanning interval. The absorption line of the gas component is modulated with a frequency ($f_0$). The modulated light is guided through the measuring gas onto a detector. A measurement signal generated by the detector is demodulated upon determining a harmonic ($nf_0$) of the frequency ($f_0$). A measurement result is produced by fitting a setpoint curve to the profile of the demodulated measurement signal. Both the demodulated measurement signal and the setpoint cure are filtered with the aid of the same filter function. The filter function is operative to suppress noise signal components of the demodulated measurement signal that disturb both signal components of the demodulated measurement signal and the setpoint curve.

2. Related Art

In EP 1 475 618 B1, a wavelength-tunable light source in the form of a laser diode generates light in the infrared region, which is led through a process gas (measuring gas) to be measured and subsequently detected. The wavelength of the light is tuned to a specific absorption line of the gas components respectively to be measured, the absorption line being scanned periodically as a function of the wavelength. To that end, the laser diode is driven with a ramp-shaped or triangular current signal within periodically sequential scanning intervals. During the comparatively slow scanning of the absorption line, the wavelength of the generated light is additionally modulated sinusoidally with high frequency and small amplitude. Since the profile of the absorption line is not linear, harmonics above the modulation frequency are also generated in the measurement signal obtained by the detector. The measurement signal is usually a modulated nth harmonic, preferably the second harmonic, demodulated by a phase-sensitive lock-in technique, and evaluated for each scanning interval to yield a measurement result. In small modulation amplitudes, the detection of the nth harmonic is directly proportional to the nth derivative of the direct measurement signal. The evaluation is performed, for example, by fitting (e.g., curve fitting) of the profile, to be expected in an ideal case, of the demodulated measurement signal (setpoint curve) to the actual profile (actual curve). Finally, the concentration of the gas component to be measured is determined from the measurement result obtained in this case.

Temperature changes within the gas analyzer can lead to changes in the measurement results. This characteristic, referred to as drift, of the gas analyzer greatly limits its measurement response and the applications to be implemented. One cause of the drift can be, inter alia, etalons in the optical beam path. The etalons lead to periodic structures in the profile of the demodulated measurement signal, wherein the structures lie in the frequency range of the absorption signal to be expected. During curve fitting, this leads to badly fitted functions and deviations of the determined concentrations from the actual concentrations of the gas component to be measured.

In order to suppress the noise signal components, it is known from the abovementioned EP 1 475 618 B1 to guide a portion of the light generated by the light source directly to a monitor detector, and to demodulate the monitor signal obtained at the nth harmonic, and evaluate it. Each deviation of the demodulated monitor signal from a zero line is based on an optical disturbance that, to the extent that it lies in the region of the light source or in the section of the beam path used in common by the measurement channel and monitor channel, also impairs the measurement signal. The disturbance is compensated by a predistortion of the driving of the light source when the wavelength of the light is additionally modulated with the nth harmonic, the modulation intensity being a function of the demodulated monitor signal.

The decoupling of a portion of the generated light on the monitor detector is, however, linked to increasing complexity of design and circuitry, which may lead to a high disturbance susceptibility. Moreover, it is not possible to compensate for disturbances of the measurement signal occurring outside the common sections of the measurement channel and monitor channel.

It is known from EP 2 336 738 A1 or EP 1 927 831 A1 to vary the optical wavelengths, for example, by mechanical vibration of the light source, and to average out the interfering periodic structures from the demodulated measurement signal. However, it is possible thereby to reduce only specific interference disturbances generated by parallel optical surfaces in the beam path.

An object of the present disclosure is reducing changes in the measurement results resulting from disturbing influences, such as, for example, temperature changes in the gas analyzer.

In accordance with an embodiment of the present disclosure, the object is achieved when both the demodulated measurement signal and the setpoint curve are filtered with the aid of the same filter function, the filter function being operative to suppress noise signal components of the demodulated measurement signal that disturb useful signal components of the demodulated measurement signals and with the setpoint curve.

If the disturbances (e.g., such as the abovementioned etalon disturbances) occur chiefly at specific frequencies, it is thus possible for them to be damped by filtering or to be removed from the demodulated measurement signal. If the spectra of the noise signal and useful signal components of the measurement signal overlap one another, the filter also influences the useful signal; put differently, the filtered useful signal changes shape due to the filtering.

Accordingly, the setpoint curve, to which fitting is to be performed, is filtered by the same filter function as the demodulated measurement signal. The filtered setpoint curve is fitted to the filtered demodulated measurement signal. An object of the filtering is to dampen the noise signal components more strongly than the useful signal components, and to achieve an improvement in the useful/noise signal ratio. This is possible in principle when the spectra of the noise signal and useful signal components are not the same. Thus, the noise signal component of an etalon is wider than the useful signal component, and therefore includes more low-frequency components than the useful signal.

According to the invention, the filter function is designed to suppress the noise signal components of the demodulated measurement signal that disturb the useful signal components of the demodulated measurement signal and with the setpoint curve. In as much as the demodulated measurement signal has previously already been filtered, the filtering has, however, been performed in a truly broadband fashion, because the spectrum changes with the width of the absorption line that, in turn, depends on the pressure. The bandwidth of the previous filtering has therefore been selected such that neither narrow nor wide demodulated measurement signals were disturbed. However, the curve fitting algorithm is scarcely disturbed by frequencies not included in the signal to be fitted, and therefore even has a good filtering effect. Thus, in contrast with the disclosed filtering, an exact fitting of the filter or the filter function to the desired function (e.g., matched filter) would lead only to slight improvements, in which case the disturbing frequencies would continue to be effective because they lie in the same region as the useful signal.

Since the disturbances occur chiefly in the low frequency region, it is preferred to use the filter function of a highpass filter. The disadvantage of the method is a lower signal-to-noise ratio at a constant ambient temperature, since signal components of the useful signal are filtered out. This reduces the temperature dependence at the expense of the limit of detection at a constant ambient temperature. However, since the temperature dependence is much larger than the noise at a constant ambient temperature, it is possible to neglect this disadvantage. Apart from that, noise can be suppressed relatively easily by averaging or Kalman filtering, whereas etalon disturbances can be removed subsequently only with difficulty.

BRIEF DESCRIPTION OF THE DRAWINGS

For the purpose of further explanation, reference is made below to the figures of the drawing.

DETAILED DESCRIPTION OF THE PRESENTLY PREFERRED EMBODIMENTS

Figure 1:
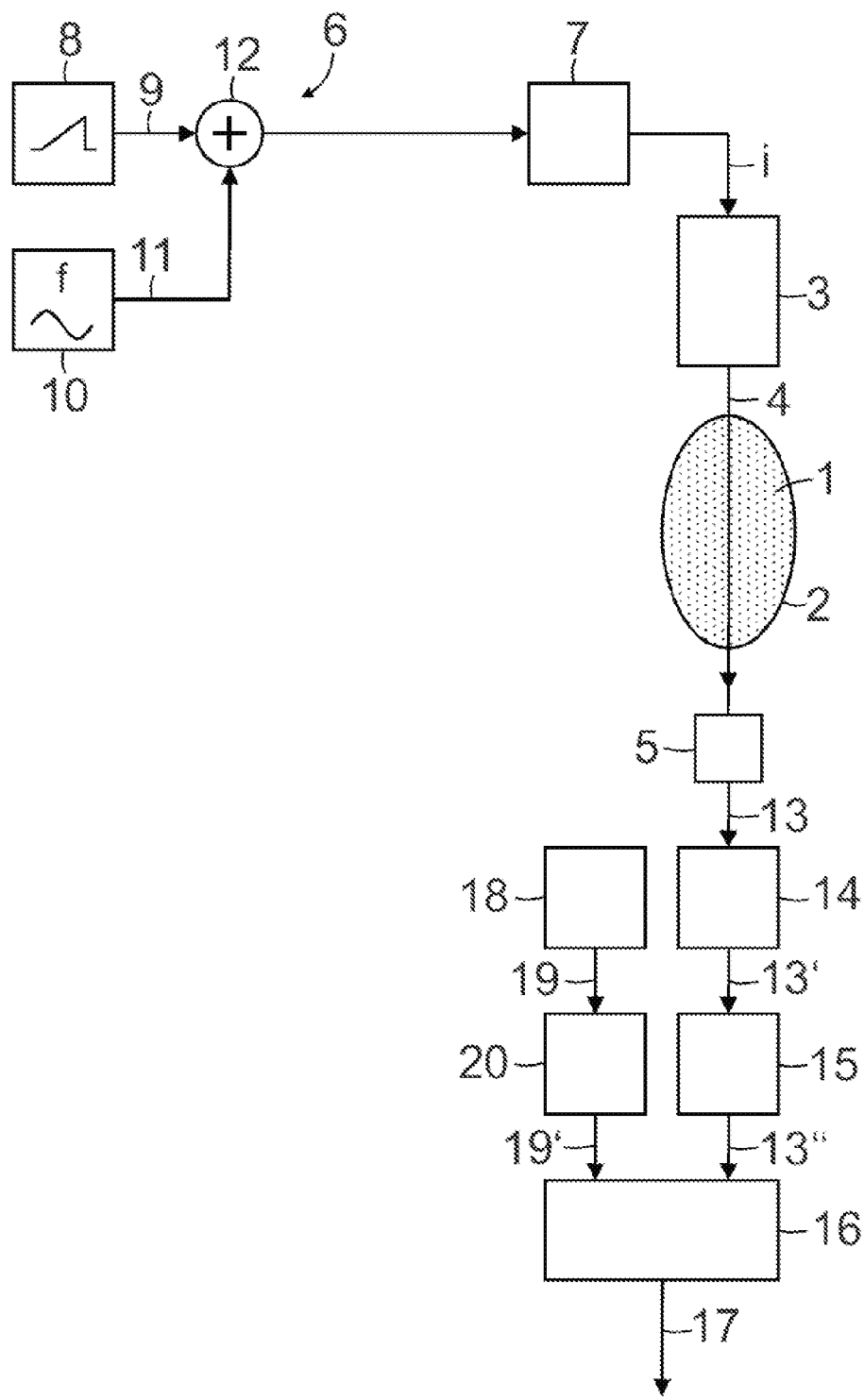
FIG. 1 shows an exemplary embodiment of a gas analyzer configured to carry out the method of an exemplary embodiment.

The gas analyzer shown in the form of a simplified block diagram in FIG. 1 is a laser spectrometer for measuring the concentration of at least one interesting gas component of a measuring gas 1 that is contained in a measuring volume 2, for example, a measuring cuvette or a process gas line. The spectrometer includes a light source 3 in the form of a laser diode whose light 4 irradiates through the measuring gas 1 to impinge on a measuring detector 5. A current source 7 controlled by a modulation device 6 feeds the laser diode 3 with an injection current i, the intensity and wavelengths of the generated light 4 being a function of the current i and the operating temperature of the laser diode 3. The modulation device 6 comprises a first signal generator 8 that drives the current source 7 periodically with a prescribed function 9, preferably a ramp-shaped or triangular one, in order to scan a selected absorption line of the interesting gas component with the aid of the wavelength of the generated light 4 that follows the profile of the current i in a more or less linear fashion. A second signal generator 10 generates a sinusoidal signal 11 of higher frequency f0 that is used in a summing element 12 to modulate the ramp-shaped or triangular function 9.

The measuring detector 5 generates, as a function of the detected light intensity, a measurement signal 13 that is demodulated in a lock-in amplifier 14 for a harmonic nf0 (n=1, 2, 3 . . . ), here, for example, 2f0, of the modulation frequency f0. The demodulated measurement signal 13' is filtered in a filter 15 with a prescribed, fixed filter function or, for example, one that can be varied as a function of temperature, in order to suppress noise signal components. In a downstream evaluation device 16, the filtered demodulated measurement signal 13" is evaluated for each scanning interval to form a measurement result 17. Provided for this purpose by a unit 18 is a setpoint curve 19, which corresponds to the ideal demodulated measurement signal 13' and is filtered in a filter 20 with the same filter function as that of the filter 15; the filtered setpoint curve 19' obtained in this case is subsequently fitted to the filtered demodulated measurement signal 13" in the evaluation device 16.

As discussed above, temperature changes within the gas analyzer can lead to drifting of the measurement results 17, one cause of drifting being etalons in the optical beam path that lead to periodic structures in the profile of the demodulated signal 13". Furthermore, the demodulated measurement signal 13" can be noisy.

Figure 2:
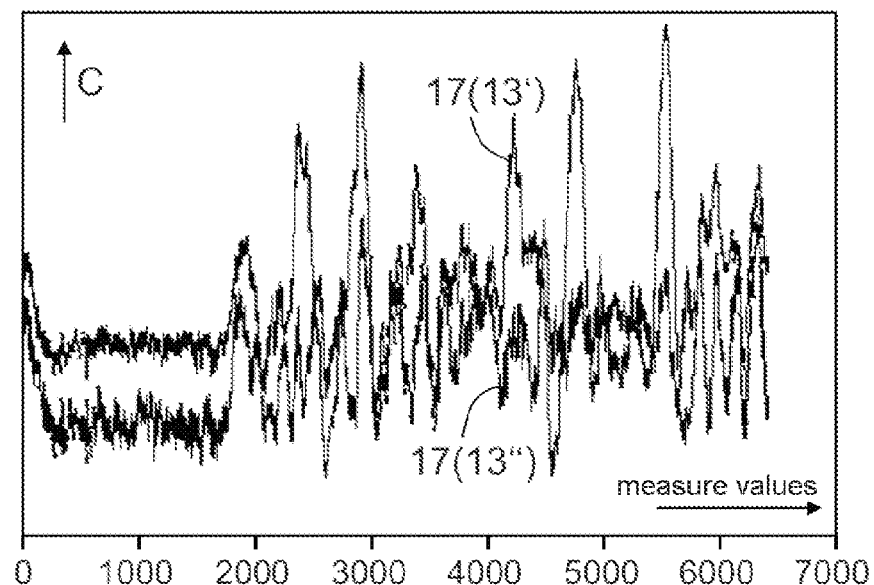
FIG. 2 shows an example of a disturbed demodulated measurement signal before and after having been filtered.

FIG. 2 shows by way of example the measurement results obtained over a series of measurements of approximately 7000 scanning intervals—here, the concentration value C of the gas component to be measured, the upper curve profile 17(13') showing the measurement results that are obtained without the inventive filtering of the demodulated measurement signal 13', and the lower curve profile 17(13") showing the measurement results that are obtained on the basis of the demodulated measurement signal 13" filtered in accordance with an embodiment (i.e., highpass filtered in this example). A first region, comprising approximately 1700 measured values is to be seen, wherein the temperature was kept constant and the measured concentration value C is substantially influenced by noise. In the adjoining region, the temperature is increased in ramp-shaped fashion, the etalon disturbances being strongly noticeable. Since the filtering discussed herein also filters away signal components of the useful signal, the noise of the filtered measurement results 17(13") is somewhat greater than that of the unfiltered measurement results 17(13'). Consequently, the temperature dependence is reduced at the expense of the limit of detection at a constant ambient temperature. However, the effect is negligible in magnitude. The noise can be suppressed relatively easily by averaging or Kalman filtering. On the other hand, the etalon disturbances are substantially less for the filtered measurement results 17(13") than for the unfiltered measurement results 17(13').

Figure 3:
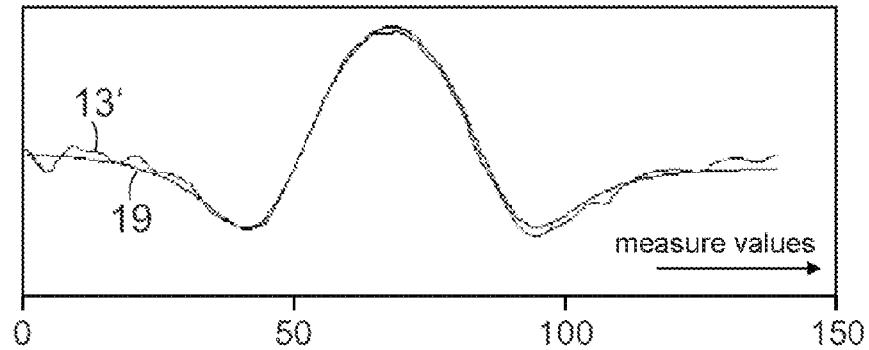
FIG. 3 shows an example of curve fitting for an unfiltered demodulated measurement signal.

FIG. 3 shows an example of the conventional fitting of the setpoint curve 19 corresponding to the ideal demodulated measurement signal 13' to the real demodulated measurement signal 13".

Figure 4:
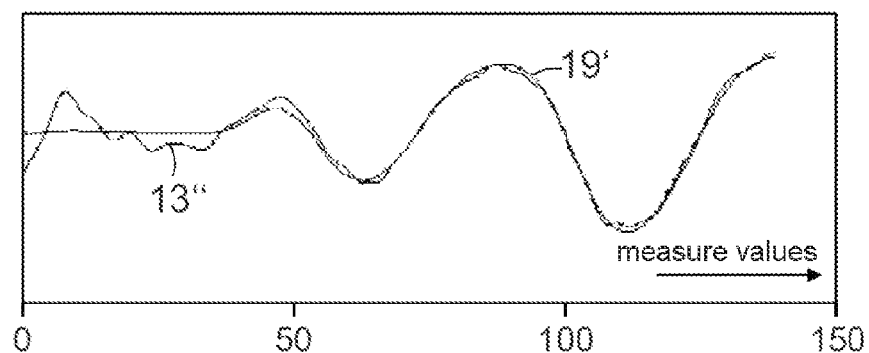
FIG. 4 shows an example of curve fitting for the filtered demodulated measurement signal.

FIG. 4 shows an example of the inventive fitting of the filtered setpoint curve 19' to the real filtered demodulated measurement signal 13".

The invention claimed is:

1. A method for measuring the concentration of a gas component in a measuring gas by a gas analyzer, the method comprising:

varying an absorption line of the gas component as a function of the wavelength of the light of a wavelength-tunable light source within a periodically sequential scanning interval;

modulating the absorption line of the gas component with a frequency ($f_o$);

guiding the modulated light through the measuring gas onto a detector;

demodulating a measurement signal generated by the detector upon determining a harmonic ($nf_0$) of the frequency ($f_0$); and producing a measurement result by fitting a setpoint curve to the profile of the demodulated measurement signal;

wherein both the demodulated measurement signal and the setpoint curve are filtered with the aid of the same filter function, the filter function being operative to suppress noise signal components of the demodulated measurement signal that disturb both signal components of the demodulated measurement signal and the setpoint curve.

2. The method of claim 1, wherein the filter function of a highpass filter is used.

* * * * *